United States Patent [19]
Grinnell et al.

[11] Patent Number: 5,741,777
[45] Date of Patent: Apr. 21, 1998

[54] MODULATION OF WOUND CONTRACTION BY BLOCKING PROTEIN TYROSINE PHOSPHATASE

[75] Inventors: Frederick L. Grinnell; Ying-Chun Lin, both of Dallas, Tex.

[73] Assignee: Board of Regents, The University of Texas System, Austin, Tex.

[21] Appl. No.: 570,615

[22] Filed: Oct. 31, 1995

[51] Int. Cl.$^6$ .......................... A61K 38/00; A61K 31/41; C07K 14/00
[52] U.S. Cl. ............................................. 514/12; 514/21
[58] Field of Search .................................. 514/12, 21

[56] References Cited

U.S. PATENT DOCUMENTS

| | | | |
|---|---|---|---|
| 4,743,442 | 5/1988 | Raaf et al. | 424/47 |
| 5,132,315 | 7/1992 | Kohn et al. | 514/359 |

OTHER PUBLICATIONS

Bell, E., Ivarsson, B. and Merrill, C. (1979) *Proc. Nat. Acad. Sci. USA* 76:1274–1278.
Bixby, J.L. and Jhabvala, P. (1992) *J. Neurobiol.* 23:468–480.
Bockus, B.J. and Stiles, C.D. (1984) *Exp. Cell Res.* 153:186–197.
Carpenter, G. and Cohen, S. (1990) *J. Biol. Chem.* 265:7709–7712.
Clark, R.A.F., Folkvord, J.M., Hart, C.E., Murray, M.J., McPherson, J.M. (1989) *J. Clin. Invest.* 84: 1036–1040.
Darby, I and Gabbiani, G. (1990) *Lab. Invest.* 63:21–29.
Eddy, R.J., Petro, J.A. and Tomasek, J.J. (1988) *Am. J. Pathol.* 130:252–260.
Edwards. J.G., Campbell, G., Grierson, A.W. & Kinn, S.R. (1991) *J. Cell Sci.* 98:363–368.
Ehrlich, H.P., Rockwell, W.B., Cornwell, T.L. and Rajaratnam, J.B.M. (1991) *J. Cell Physiol.* 146:1–7.
Fischer, E.H., Charbonneau, H. and Tonks, N.K. (1991) *Science* 253:401–406.
Gordon, J.A. (1991) *Meth. Enzymol.* 201:477–482.
Grinnell, F. (1994) *J. Cell Biol.* 124:401–404.
Guidry, C. and Grinnell, F. (1985) *J. Cell Sci.* 79:67–81.
Gullberg, D., Tingstrom A., Thuresson, A-C., Olsson, L., Terracio, L., Borg, T.K. and Rubin, K. (1990) *Exp. Cell Res.* 186:264–272.
Hammacher, A., Mellstrom, K. Heldin, C-H. and Westermark, B. (1989) *EMBO J.* 8:2489–2495.
Hedberg, K.M., Bengtsson, T., Safiejko-Mroczka, B., Bell, P.B. and Lindroth, M. (1993) *Cell Motil & Cyto.* 24:139–149.
Heffetz, D., Rutter, W.J. and Zick, Y. (1992) *Biochem. J.* 288:631–635.
Herman, B. and Pledger, W.J. (1985) *J. Cell Biol.* 100:1031–1040.
Hordijk, P.L., Verlaan, I., Van Corven, E.J. and Moolenaar, W.H. (1994) *J. Biol. Chem.* 269:645–651.

Kolodney, M.S. and Elson, E.L. (1993) *J. Biol. Chem.* 268:23850–23855.
Kolodney, M.S. and Wysolmerski, R.B. (1992) *J. Cell Biol.* 117:73–82.
Laemmli, U.K. (1970) *Nature* 227:680–685.
Lee, T-L., Lin, Y-C., Mochitate, K. and Grinnell, F. (1993) *J. Cell Sci.* 105:165–177.
Lin, Y-C. and Grinnell, F. (1993) *J. Cell Biol.* 122:663–672.
Madsen, K.L., Ariano, D., and Sedorak, R.N. (1995) *Diabetologia* 38:403–412.
Mast, B.A. (1992) In: *Wound Healing: Biochemical and Clinical Aspects*. Ed: I.K. Cohen, RF Dieglemann, and WJ Lindblad, W.B. Saunders Co., Philadelphia, PA, pp. 344–355.
Mellstrom, K., Heldin, C–H. and Westermark, B. (1988) *Exp. Cell Res.* 177:347–359.
Mochitate, K. Pawelek, P. and Grinnell, F. (1991) *Exp. Cell Res.* 193:198–207.
Morgan, C.J. and Pledger, W.J. (1992) In: *Wound Healing: Biochemical and Clinical Aspects*. Ed: IK Cohen, RF Diegelmann, and WJ Lindblad, W.B. Saunders Co., Philadelphia, PA, pp. 63–76.
Nakagawa, S., Pawelek, P. and Grinnell, F. (1989) *J. Invest. Dermatol* 93:792–798.
Nishiyama, T., Akutsu, N., Horii, I., Nakayama, Y., Ozawa, T. and Hayashi, T. (1991) *Matrix* 11:71–75.
Parker, R.D., and Sharma, R.P. (1978) *Jrnl. of Envir. Ethol and Tox.* 2:235–245.
Rankin, S. and Rozengurt, E. (1994) *J. Biol. Chem.* 269:704–710.
Ridley, A.J. and Hall, A. (1992) *Cell* 70:389–399.
Ridley, A.J. and Hall, A. (1994) *EMBO J.* 13:2600–2610.
Roeckel, D. and Krieg, T. (1994) *Exp. Cell Res.* 211:42–48.
Rudolph, R., Berg, J.V. and Ehrlick, H.P. (1992) In: *Wound Healing: Biochemical abd Clinical Aspects*. Ed: IK Cohen, RF Diegelmann, and WJ Lindblad, W.B. Saunders Co., Philadelphia, PA, pp. 96–114.
Seufferlein, T. and Rozengurt, E. (1994) *J. Biol. Chem.* 269:9345–9351.
Skalli, O. and Gabbiani, G. (1988) In: *The Molecular and Cellular Biology of Wound Repair*. Ed: RAF Clark and PM Henson, Plenum Press NY, pp. 373–402.
Tidball, J.G. and Spencer, M.J. (1993) *J. Cell Biol.* 123:627–635.

(List continued on next page.)

*Primary Examiner*—Cecilia J. Tsang
*Assistant Examiner*—P. Lynn Touzeau
*Attorney, Agent, or Firm*—Arnold, White & Durkee

[57] ABSTRACT

The present invention relates generally to methods and compositions for inhibiting wound contraction and the scarring that frequently results from such contraction. More particularly, the invention relates to the use of a protein tyrosine phosphatase inhibitor to block the dephosphorylation of protein tyrosine phosphatase receptors and interrupt the cyclic nature of wound contraction.

10 Claims, 3 Drawing Sheets

OTHER PUBLICATIONS

Tingstrom, A., Heldin, C–H. and Rubin, K. (1992) *J. Cell Sci.* 102:315–322.

Tomasek, J.J., Haaksma, C.J., Eddy, R.J. and Vaughan, M.B. (1992) *Anatomical Record* 232:359–368.

Ullrich, A. and Schlessinger, J. (1990) *Cell* 61:203–212.

Vogel, A., Raines, E., Kariya, B., Rivest, M.J. & Ross, R. (1978) *Proc. Natl. Acad. Sci. USA* 75:2810–2814.

Volberg, T., Zick, Y., Dror, R., Sabanay, I., Gilon, C., Levitzki, A. and Geiger, B. (1992) *EMBO J.* 11:1733–1742.

Welch, M.P., Odland, G.F. and Clark, R.A.F. (1990) *J. Cell Biol.* 110:133–145.

Zippel et al, European J. Cell Biology, Dec., 50(2); 424–34 (1989). Abstract.

Gentleman et al., Biochem. Biophys Acta, 798(1);53–59 (1984) Abstract.

MODULATION OF WOUND CONTRACTION BY BLOCKING PROTEIN TYROSINE PHOSPHATASE

FIELD OF THE INVENTION

The present invention relates generally to methods and compositions for inhibiting wound contraction and the scarring that frequently results from such contraction. More particularly, the invention relates to the use of a protein tyrosine phosphatase inhibitor to block the dephosphorylation of protein tyrosine phosphatase receptors and interrupt the cyclic nature of wound contraction.

BACKGROUND OF THE INVENTION

Wound contraction can result in significant scarring and loss of physiological function. This can be particularly severe for surgical and burn patients. Consequently, there has been considerable interest in understanding the mechanism of contraction and particularly, its regulation. Protein tyrosine phosphatases have been identified as agents involved in such regulation. These phosphatases are thought to work in conjunction with tyrosine kinases in stimulating wound contraction and cell growth.

Tyrosine kinases are major stimulators of cell growth and most likely, wound contraction. Such stimulation depends on the ability of these kinases to attach phosphate groups to tyrosine residues on proteins. However, proper stimulation also requires that phosphate residues be removed from the receptors and then reattached in a cyclic fashion. Tyrosine phosphatases, a diverse group of cytoplasmic and transmembrane enzymes remove the phosphates.

Interruption of this cycle through inhibition of tyrosine phosphatases thus appears a promising means of regulating wound contraction. Such a means of inhibiting wound contraction would enhance considerably or even supplant the limited mechanical and surgical means of intervention currently available.

In addition to reversing the effects of tyrosine kinases, tyrosine phosphatases are believed to constitute a novel class of receptors that make up an independent signaling pathway in the cell. (Campbell et al., 1991; Bixby et al., 1992) Specifically, the tyrosine phosphatases are also major regulators of cell growth. Thus, the inhibition of these enzymes very likely will play a major role in the regulation of uncontrolled cell growth or cancer development.

SUMMARY OF THE INVENTION

The present invention seeks to regulate wound contraction. Specifically, the invention provides methods and compositions for inhibiting wound contraction.

The inventors have discovered through the use of in vitro models that the inhibition of tyrosine phosphatases inhibits wound contraction. For example, when human fibroblasts are cultured in an anchored collagen matrix, they reorganize the matrix and develop stress. Upon experimental release of the matrix, the cells contract the matrix. It has been found that treatment of fibroblasts in stressed collagen matrices with vanadate, a protein tyrosine phosphatase inhibitor, and platelet-derived growth factor (PDGF) in serum-containing medium inhibits the ability of cells to contract the matrix.

Vanadate/PDGF/serum stimulation did not block contraction immediately but rather resulted in the generation of an inhibitory signal that developed over a period of 80 minutes. The signal was highly specific since other factors such as lysophosphatidic acid and epidermal growth factor were unable to replace PDGF or serum. The presence of vanadate also blocked dephosphorylation of tyrosine-phosphorylated-PDGF receptors after PDGF/serum stimulation and caused accumulation of tyrosine-phosphorylated proteins in the cells.

In parallel experiments, fibroblasts in monolayer culture were found to undergo reorganization of their actin cytoskeleton when treated with vanadate in the presence of PDGF and serum-containing medium. These results suggest that a tyrosine-phosphorylated signaling pathway is important in the regulation of wound contraction. Thus, inhibiting such a pathway, and in particular, inhibiting the dephosphorylation of tyrosine-phosphorylated PDGF receptors is a promising means of inhibiting wound contraction and consequent scarring. In addition, because of the involvement of tyrosine kinases and tyrosine phosphatases in the regulation of cell growth, inhibition of tyrosine phosphatases is likely a promising means of inhibiting cell growth in general.

Given these discoveries and the need to reduce post-surgical and post-injury scarring, the present inventors have conceived of and developed the following embodiments of the present invention.

In one embodiment, the present invention provides a method of inhibiting wound contraction in an animal. Wound contraction at too fast a pace can lead to unsightly scarring in surgical and burn patients. The method involves inhibiting wound contraction by administering to the wound a therapeutically effective mount of a tyrosine phosphatase inhibitor.

A therapeutically effective mount is that amount necessary to reproducibly reduce the amount of wound contraction in a healing patient. Reduction of the amount of wound contraction includes both reducing the amount of puckering and scarring that frequently occurs in the tissue surrounding a wound and also slowing the rate of contraction of the wounded tissue itself.

In a preferred embodiment, the tyrosine phosphatase inhibitor is a salt of vanadate, for example, sodium vanadate.

The tyrosine phosphatase inhibitor of the present invention can be administered to the wound in several ways. For instance, the inhibitor can be administered topically, parenterally, or orally. For administration to a patient, a therapeutically effective amount of the tyrosine phosphatase inhibitor of the present invention will preferably be dispersed in a pharmacologically acceptable carrier. The particular carrier chosen will depend upon whether the inhibitor is to be administered topically, parenterally, or orally. Optimally, a therapeutically effective amount of the tyrosine phosphatase inhibitor will be that amount required to achieve a blood serum level of between 3.0 and 15.0 µM (micromolar). For instance, this would require an oral or parenteral dose of approximately between 0.1–1.0 mg of $Na_3VO_4$ (sodium vanadate) per ml of carrier material. (Madsen et al., 1995). A typical topical dose is approximately 0.1–1.0 mM (millimolar) as evidenced by the in vitro studies of the present invention.

In another embodiment, the invention provides a pharmaceutical composition composed of a therapeutically effective amount of a tyrosine phosphatase inhibitor dispersed in a pharmacologically acceptable carrier.

In a preferred version of that embodiment, the tyrosine phosphatase inhibitor is a salt of vanadate.

In yet another embodiment, the invention provides a method of blocking the dephosphorylation of tyrosine receptors. This method involves exposing an effective amount of a tyrosine phosphatase inhibitor to the receptors in the presence of serum and platelet derived growth factor.

Vanadate inhibits tyrosine phosphatase activity by preventing the dephosphorylation of tyrosine phosphorylated platelet-derived growth factor (PDGF) receptors and similar receptors on the surface of other proteins involved in the PDGF signaling pathway. In an in vitro model used to study wound contraction, a stressed collagen matrix, PDGF and serum is required for the inhibition of contraction. For in vivo activity, PDGF and serum need not be separately administered since those compounds are present in an animal body at a sufficient concentration.

In a preferred embodiment, the tyrosine phosphatase inhibitor is a salt of vanadate, such as sodium vanadate. Alternatively, a salt of molybdate may be utilized.

Where the tyrosine phosphatase inhibitor is used to block the dephosphorylation of tyrosine phosphatase receptors in vitro, such as for use in a quantitative assay, it is preferred that serum be present in the medium at a concentration of between approximately 0.5 percent and 10 percent. Most preferably, protein tyrosine phosphatase inhibitor should be exposed to said receptors in a medium in which the serum concentration is approximately 10 percent.

In a most preferred embodiment where the tyrosine phosphatase inhibitor is used to block the dephosphorylation of protein tyrosine phosphatase in vivo, a therapeutically effective amount of the inhibitor is dispersed in a pharmacologically acceptable carrier. The particular carrier chosen will depend upon whether the inhibitor is manufactured for topical, parenteral, or oral administration.

Optimally, a therapeutically effective amount of the tyrosine phosphatase inhibitor will be that amount required to achieve a blood serum level of between 3.0 and 15.0 µM (micromolar). For instance, this would require an oral or parenteral dose of approximately between 0.1–1.0 mg of $Na_3VO_4$ (sodium vanadate) per ml of carrier material. (Madsen et al., 1995). A typical topical dose is approximately 0.1–1.0 mM (millimolar) as evidenced by the in vitro studies of the present invention.

In still another embodiment, the present invention provides a method of inhibiting fibroblast contraction in a collagen matrix. This method involves exposing an effective amount of tyrosine phosphatase inhibitor to the matrix in the presence of serum and platelet-derived growth factor.

In a preferred version of this embodiment, the tyrosine phosphatase inhibitor is a salt of vanadate such as sodium vanadate.

Where the tyrosine phosphatase inhibitor is used to inhibitor fibroblast contraction in a collagen matrix in vitro, such as for use in a quantitative assay, it is preferred that serum be present in the medium at a concentration of between approximately 0.5 percent and 10 percent. Most preferably, the tyrosine phosphatase inhibitor should be exposed to the matrix in a medium in which the serum concentration is approximately 10 percent.

For administration to a patient, a therapeutically effective amount of the tyrosine phosphatase inhibitor of the present invention will preferably be dispersed in a pharmacologically acceptable carrier. The particular carrier chosen will depend upon whether the inhibitor is manufactured for topical, parenteral or oral administration.

Optimally, a therapeutically effective amount of the tyrosine phosphatase inhibitor will be that amount required to achieve a blood serum level of between 3.0 and 15.0 µM (micromolar). For instance, this would require an oral or parenteral dose of approximately between 0.1–1.0 mg of $Na_3VO_4$ (sodium vanadate) per ml of carrier material. (Madsen et al., 1995). A typical topical dose is approximately 0.1–1.0 mM (millimolar) as evidenced by the in vitro studies of the present invention.

In yet a final embodiment, the present invention provides a method of inhibiting cell growth in an animal. This method involves administering to an animal a therapeutically effective amount of a protein tyrosine phosphatase inhibitor.

The tyrosine phosphatases are multi-faceted enzymes. That is, they do not function merely to act as helpers for the tyrosine kinases. Rather, they constitute a novel class of receptors that make up important signaling pathways in cells related to cell growth, adhesion and cell spreading (Campbell et al., 1991). Thus, inhibition of these phosphatases with an inhibitor such as vanadate offers a promising means of controlling abnormal cell growth such as cancer.

For use in controlling cell growth a preferred tyrosine phosphatase inhibitor is a salt of vanadate such as sodium vanadate. Alternatively, a salt of molybdate maybe utilized.

For administration to a patient, a therapeutically effective amount of the tyrosine phosphatase inhibitors of the present invention will preferably be dispersed in a pharmacologically acceptable carrier. The particular carrier chosen will depend upon whether the inhibitor is manufactured for topical, parenteral or oral administration.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENT

Wound contraction plays a major role in wound repair by pulling together the margins of open wounds (Peacock, 1984; Clark, 1988; and Mast, 1992). Smooth muscle-like cells called myofibroblasts generate the force of contraction (Skalli et al., 1988; and Rudolph et al, 1992). These cells, which express α-smooth muscle actin, are derived from fibroblasts adjacent to the wounded tissue (Eddy et al., 1988; Darby et al., 1990; and Welch et al., 1990).

Wound contraction can be studied in vitro utilizing fibroblasts cultured in anchored collagen matrices. The fibroblasts reorganize collagen as they attempt to move through the matrix, a process called tractional remodeling (Harris et al., 1981). As matrix reorganization progresses, the cells develop stress fibers similar to myofibroblasts (Mochitate et al., 1991; Tomasek et al., 1992; and Lee et al., 1993). Subsequently, when the matrix is released experimentally, the cells undergo contraction during which their stress fibers shorten and disappear (Tomasek et al., 1992; and Lee et al., 1993).

After fibroblasts contract stressed collagen matrices, cell proliferation ceases and cells become quiescent within a short time (Mochitate et al., 1991). Development of quiescence has been found to occur, at least in part, because of changes in cell responsiveness to platelet-derived growth factor (PDGF). The cells become less responsive to PDGF (Nakagawa et al., 1989; and Nishiyama et al., 1991), show decreased PDGF-induced receptor aggregation (Tringstrom et al., 1992), and loss of PDGF receptor signaling capacity (Lin et al., 1993).

In order to show that human fibroblast contraction can be inhibited by blocking the action of protein tyrosine phosphatase, human fibroblasts were treated with the tyrosine phosphatase inhibitor, sodium vanadate, and PDGF in serum-containing medium. This treatment inhibited the cells' ability to contract stressed collagen matrices. The presence of vanadate, also prevented dephosphorylation of tyrosine-phosphorylated PDGF receptors and other p-Tyr-proteins in the PDGF signaling pathway. In parallel studies, treatment of fibroblasts in monolayer culture with vanadate/PDGF/serum resulted in cytoskeletal reorganization and disappearance of actin stress fibers.

Vanadate/PDGF/serum stimulation does not block contraction immediately, but rather resulted in the generation of an inhibitory signal that developed over a period of 80 minutes. The signal was highly specific since other factors such as lysophosphatidic acid and epidermal growth factor were unable to replace PDGF or serum.

Inhibition of matrix contraction provides another instance of a cell-adhesion related process that can be inhibited by a protein tyrosine phosphatase inhibitor such as vanadate. Other examples, however, include cell spreading (Edwards et al., 1991), disassembly of adherent junctions (Volberg et al., 1992), and prevention of neurite elongation (Bixby et al., 1992). Importantly, because tyrosine kinases and protein tyrosine phosphatases in conjunction are major stimulators of cell growth, it is believed that protein tyrosine phosphatase inhibitors such as vanadate may be useful in inhibiting the growth of tumor cells.

Under conditions resulting in inhibition of matrix contraction, vanadate/PDGF/serum treatment also blocked dephosphorylation of p-Tyr-PDGF receptors and permitted rapid accumulation of a large number of p-Tyr-proteins, which were undetectable in the absence of vanadate. These finding are consistent with the ability of vanadate to block protein tyrosine phosphatases (Gordon, 1991; and Heffetz et al., 1992), and suggest that normal turnover of p-Tyr intermediates is required for contraction to occur. Little is known about p-Tyr signaling pathways during fibroblast contraction, but phosphorylation of focal adhesion kinase has been detected when fibroblasts are cultured in collagen matrices (Roeckel et al., 1994).

Parallel to the experiments on collagen matrix contraction, the effects of vanadate/PDGF/serum on the cytoskeleton of human fibroblasts attached to culture dishes was studied. Previously, it was shown that PDGF treatment of human fibroblasts caused redistribution of actin into lamellar membrane ruffles along the cell margins and circular ruffles on the dorsal cell surface (Mellstrom et al., 1988; Hammacher et al., 1989; and Hedberg et al., 1993), and vanadate treatment of baby hamster kidney cells has been shown to cause redistribution of F-actin into structures called podosomes (Marchisio et al., 1988). Lamellar ruffling alone was observed, perhaps because human fibroblasts were cultured in 1% serum whereas others used serum-starved human fibroblasts that had been cultured without serum (Mellstrom et al., 1988; Hammacher et al., 1989; and Hedberg et al., 1993).

Disruption of actin stress fibers required combined treatment of cells with vanadate/PDGF/serum. In addition, the time required for disruption of actin stress fibers correlated with the time required for inhibition of matrix contraction. Moreover, vanadate/PDGF/serum also resulted in rapid reorganization of tyrosine phosphorylated proteins within 20 minutes and some association of these molecules with actin stress fibers. This is consistent with the theory that intermediates in the p-Tyr signaling pathway regulate activity of the cytoskeleton. Treatment of cells with vanadate for 80 minutes in the absence of PDGF also resulted in increased association of p-Tyr molecules with cell cytoskeletal components, although actin stress fiber disruption was not observed.

Previous studies have shown that PDGF can have markedly different effects on the cell cytoskeleton depending on actin organization of the cells. For instance, PDGF promotes actin stress fiber formation in serum-deprived Swiss 3T3 fibroblasts, which lack stress fibers (Ridley et al., 1994; Ridley et al., 1992; and Rankin et al., 1994). On the other hand, PDGF was reported to cause transient cytoskeleton disruption of growth-arrested L6 myofibroblasts and BALB/c-3T3 fibroblasts, which have prominent actin stress fibers (Bockus et al., 1984; Herman et al., 1985; and Tidball et al., 1993). In the case of human fibroblasts, which also have prominent stress fibers, PDGF treatment also caused disruption of the actin cytoskeleton in the presence of vanadate as already discussed.

The different PDGF responses described above may help explain the observation that PDGF can stimulate contraction of floating but not stressed collagen matrices. Fibroblasts in floating collagen matrices lack stress fibers and have only an actin filament meshwork (Bell et al., 1979; Grinnell, 1994; Harris et al., 1981). In this case, PDGF may enhance cytoskeletal activity resulting in increased matrix contraction. Fibroblasts in stressed collagen matrices, on the other hand, have prominent actin stress fibers (Mochitate et al., 1992; Tomasek et al., 1992; and Lee et al., 1993). And in this case, combined PDGF/vanadate/serum treatment appeared to inhibit cytoskeletal activity resulting in decreased matrix contraction. The difference in signaling responses involved in contraction of stressed vs. floating collagen matrices may also account for the ability of vanadate to inhibit contraction of floating but not stressed collagen matrices in the absence of PDGF.

Inhibition of Stressed Collagen Matrix Contraction

Figure 1:
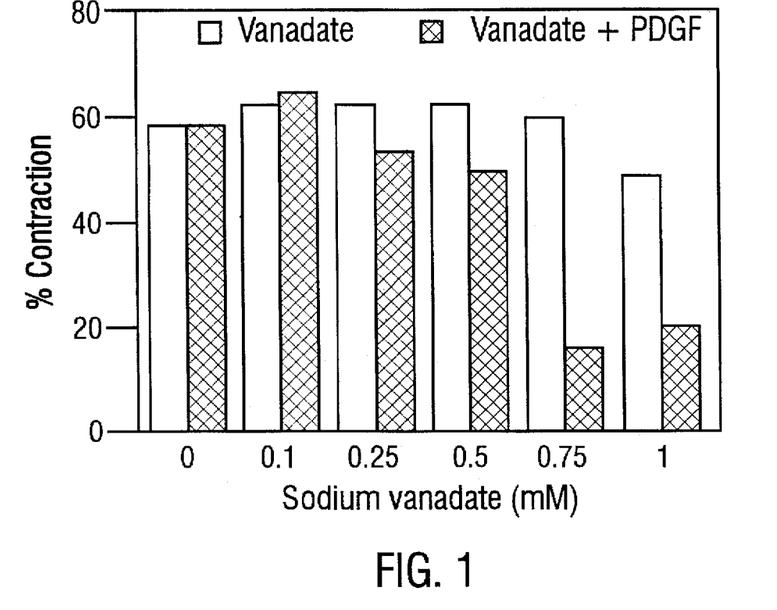
FIG. 1 is a bar chart illustrating the percent inhibition of contraction of stressed collagen matrices at varying concentrations of vanadate and platelet-derived growth factor.

FIG. 1 illustrates that fibroblast contraction of stressed collagen matrices in medium consisting of Dulbecco's modified Eagles's medium (DE) and 10% fetal bovine serum, (FBS) resulted in a 60% decrease in matrix diameter during the first hour following release of the matrices from the underlying culture dish. Addition of 50 ng/ml PDGF, the concentration required for maximal receptor autophosphorylation by fibroblasts in stressed collagen matrices (Lin et al., 1993), had no detectable effect on contraction. That is PDGF does not stimulate contraction of stressed matrices. However, as discussed, PDGF is required in conjunction with vanadate to inhibit contraction. Addition of vanadate up to 1 mM also had little effect on contraction although this concentration inhibited protein tyrosine phosphatase (PTPase) activity. If, however, cells were treated with a combination of 50 ng/ml PDGF and 0.75 mM vanadate or higher, matrix contraction was reduced from 60% to 20%. Reduction to 20% amounts to almost complete inhibition of the active cellular contribution to contraction since stressed collagen matrices contract 15–20% after they are released as a result of elastic recoil (Tomasek et al., 1992).

In order to distinguish whether the inhibitory effect of vanadate/PDGF treatment occurred before or after initiation of contraction, studies were carried out using separate pretreatment and contraction periods. Fibroblasts in anchored matrices were pretreated with sodium vanadate and PDGF in DME/10% FBS. After 20 minutes, the cultures were washed and switched to DME/10% FBS lacking vanadate/PDGF before contraction was initiated by releasing the matrices. The set of graph bars labeled (A) in FIG. 2 illustrate that under these conditions, there was little inhibition of matrix contraction.

Figure 2:
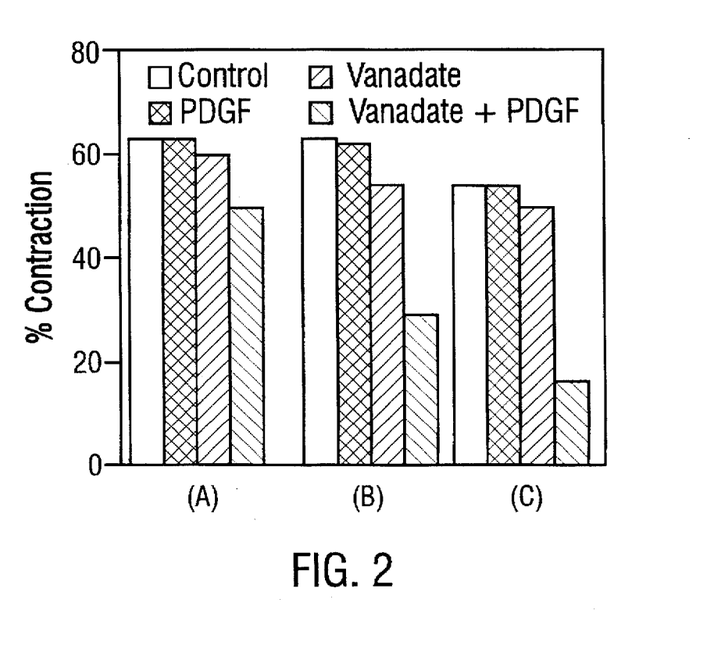
FIG. 2 is a bar chart illustrating the lag time period required for contraction of stressed collagen matrices in the presence of vanadate and platelet-derived growth factor.

As shown by the set of graph bars labeled (B) in FIG. 2, on the other hand, when the pretreatment period with vanadate/PDGF was extended from 20 minutes to 80 minutes before the cultures were washed of vanadate/PDGF, the inhibition of contraction was greater. Furthermore, in this case, subsequent contraction was inhibited even in the absence of vanadate/PDGF in the contraction medium. Finally, the set of graph bars labeled (C) in FIG. 2 show that a 20 minute pretreatment period with vanadate/PDGF followed by an additional 60 minute pretreatment in medium lacking vanadate/PDGF also was sufficient to cause inhibition of subsequent contraction when the matrices were released. Taken together, these results show that vanadate/PDGF treatment generated a signal prior to contraction that interfered with the subsequent ability of cells to contract the matrix.

Figure 3:
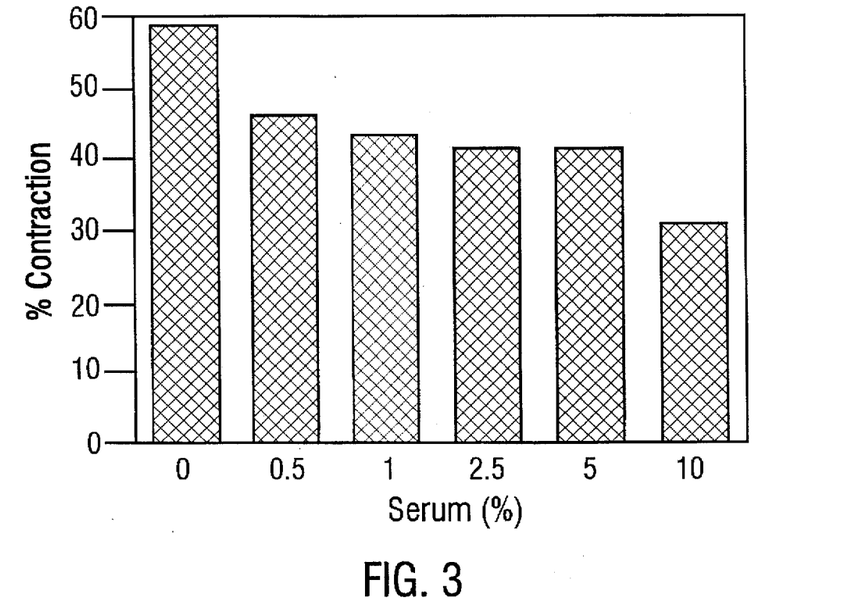
FIG. 3 is a bar chart illustrating percent contraction of stressed collagen matrices at varying serum concentrations.

Further studies were carried out to test whether serum was necessary for the vanadate/PDGF-induced signal during the pretreatment period. In these experiments, fibroblasts were pretreated for 80 minutes with vanadate, PDGF, and varying serum concentrations. Then the cells were washed into fresh medium lacking vanadate and PDGF but containing 10% FBS. Addition of serum during the contraction period is necessary because fibroblasts are unable to contract stressed collagen matrices in the absence of serum factors. As can be seen in FIG. 3, vanadate/PDGF pretreatment did not generate the inhibitory signal when serum was omitted from the pretreatment incubation event though serum was present during the subsequent contraction period. Generation of the inhibitory signal occurred partially with 0.5% FBS in the medium and maximally with 10% FBS.

Figure 4:
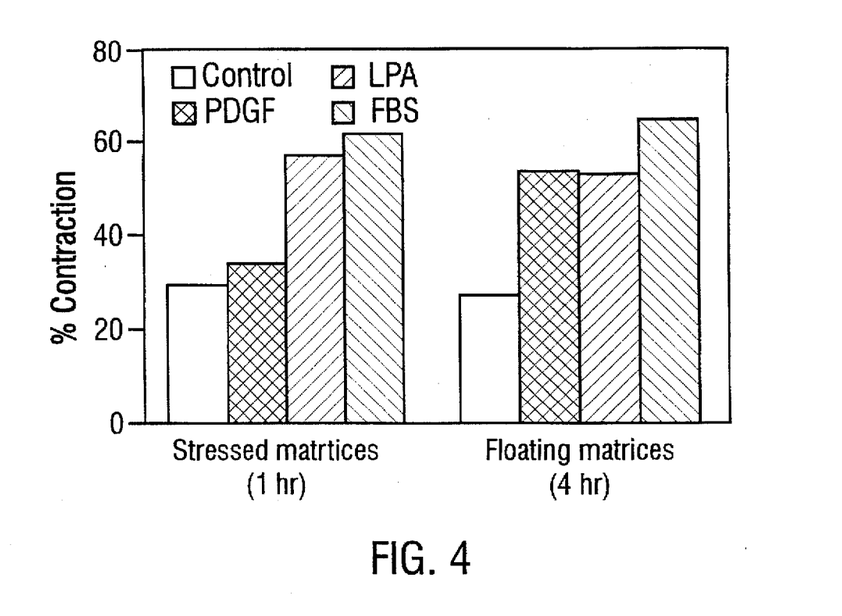
FIG. 4 is a bar chart illustrating the effect of serum, lysophosphatidic acid, and platelet-derived growth factor on contraction of both stressed and floating collagen matrices.

The specificity of the signaling process resulting in inhibition of contraction was tested by studying the ability of two other signaling molecules, epidermal growth factor and lysophosphatidic acid, to substitute for PDGF or serum during the pretreatment, as opposed to the contraction, period. Like PDGF, epidermal growth factor (EGF) activates a tyrosine kinase signaling pathway (Carpenter et al., 1990; and Ullrich et al., 1990) and can substitute for serum when combined with PDGF to promote cell proliferation. Also, EGF treatment stimulates EGF receptor autophosphorylation by fibroblasts in collagen matrices (Lin et al., 1993). Lysophosphatidic (LPA) acid activates several signaling events including tyrosine phosphorylation of focal adhesion kinase (FAK) (Ridley et al., 1994; Hordijk et al., 1994; Seufferlein et al., 1994; and Saville et al., 1994) and can stimulate assembly of stress fibers under some conditions (Ridley et al., 1992). FIG. 4 illustrates that lysophosphatidic acid can be substituted for FBS in the pretreatment period to stimulate contraction of stressed matrices.

Figure 5:
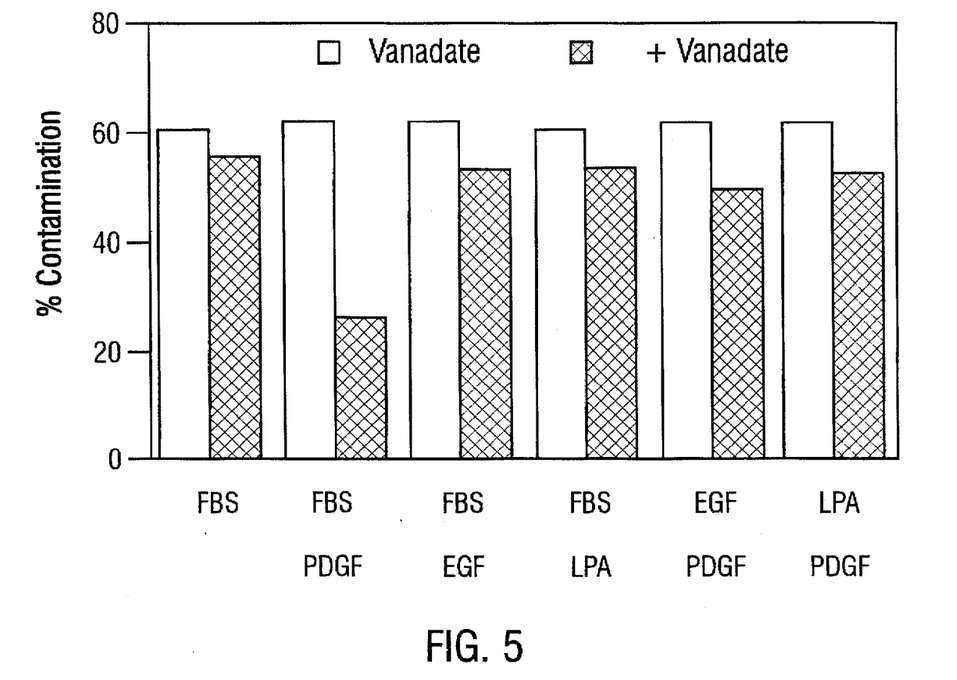
FIG. 5 is a bar chart illustrating the specificity of inhibition of stressed collagen matrices in response to fetal bovine serum, platelet-derived growth factor, epidermal growth factor, and lysophosphatidic acid.

FIG. 5 shows the specificity of inhibition of contraction of stressed matrices. Specifically, maximal inhibition of contraction occurred when vanadate and PDGF were used together, indicating that generation of the signal for inhibition of fibroblast contraction involved a unique signalling pathway.

Inhibition of Floating Matrix Contraction

The ability of vanadate to inhibit contraction of floating collagen matrices was also tested. Contraction of floating versus stressed collagen matrices involves somewhat different mechanisms based on differences in cytoskeletal organization of cells in the matrices (Grinnell, 1994) and differences in growth factor responsiveness (Kolodney, et al., 1992; kolodney et al., 1993; Pilcher et al., 1994; Clark et al., 1989; and Gullberg et al., 1990). That is, as shown in FIG. 4, PDGF can substitute for serum or lysophosphatidic acid in promoting contraction of floating collagen matrices but not stressed matrices.

The different PDGF responses described above may help explain the observation by us and others (Pilcher et al., 1994; Clark et al., 1989; and Gullberg et al., 1990) that PDGF can stimulate contraction of floating but not stressed collagen matrices. Fibroblasts in floating collagen matrices lack stress fibers and have only an actin filament meshwork (Bell et al., 1979; Grinnel, 1994; and Harris et al., 1981). In this case, PDGF may enhance cytoskeletal activity resulting in increased matrix contraction. Fibroblasts in stressed collagen matrices, on the other hand, have prominent actin stress fibers (Mochitate et al., 1991; Tomasek et al., 1992; and Lee et al., 1993). And in this case, combined PDGF/vanadate/serum treatment appeared to inhibit cytoskeletal activity resulting in decreased matrix contraction. The difference in signaling responses involved in contraction of stressed versus floating collagen matrices may also account for the ability of vanadate to inhibit contraction of floating but not stressed collagen matrices in the absence of PDGF.

Figure 6:
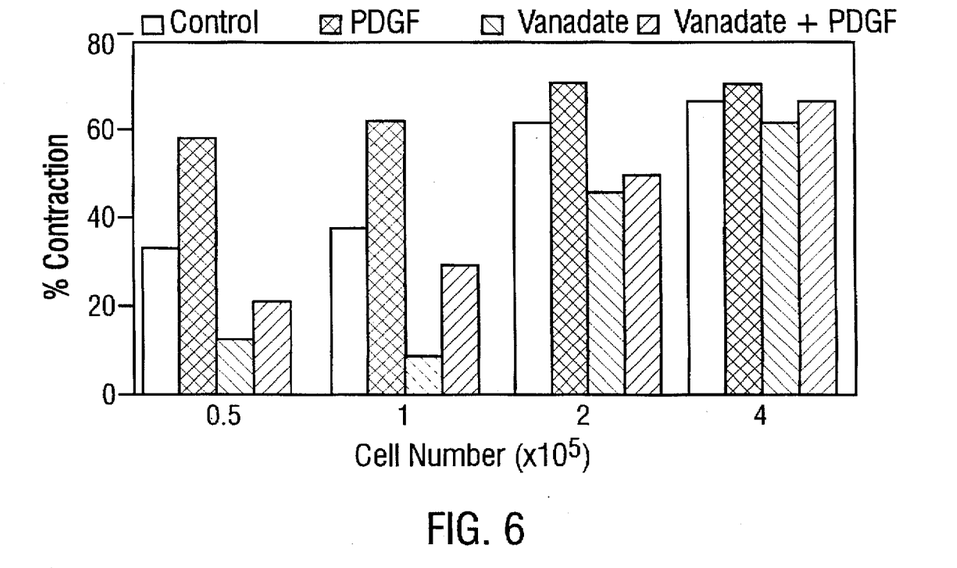
FIG. 6 is a bar chart illustrating the dependence of inhibition of contraction of floating matrices on fibroblast cell number, platelet-derived growth factor and vanadate.

FIG. 6 shows the effects of PDGF and vanadate on contraction of floating collagen matrices in serum-containing medium. With equivalent cell numbers, contraction of floating matrices occurs more slowly than that of stressed matrices. Therefore, cell number was varied to obtain a range of contraction rates. Rather than increase vanadate inhibition of contraction as was observed for stressed matrices, the addition of PDGF enhanced the extent of contraction itself.

Effect of Vanadate on Tyrosine Phosphorylation

It seems likely that p-Tyr intermediates in the PDGF/serum signaling pathway accumulate in the presence of vanadate. To confirm this studies were carried out analyzing p-Tyr protein phosphorylation by fibroblasts stimulated with vanadate/PDGF/serum. Specifically, the profile of tyrosine phosphorylated proteins in fibroblasts in stressed collagen matrices after pretreatment with and without vanadate and PDGF in medium containing 10% FBS was compared. Tyrosine phosphorylated proteins were identified by immunoblotting with anti-p-Tyr monoclonal antibody.

Changes in phosphotyrosine protein profile were studied. Sodium vanadate (1 mM) was added as indicated to fibroblasts in stressed collagen matrices in DME/10% FBS. Ten minutes after addition of vanadate, 50 ng/ml PDGF-BB was added to the designated samples. After a total incubation of 20 minutes or 80 minutes, the samples were extracted and subjected to immunoblotting with anti-p-Tyr monoclonal antibodies. FBS was CM-Sephadex treated.

Control cells (-vanadate, -PDGF) showed low levels of phosphorylation of 60 kDa, 125 kDa, and 180 kDa molecules. Addition of PDGF resulted in phosphorylation of the 180 kDa PDGF receptor. In the absence of vanadate, the phosphorylation of PDGF receptor was higher after 20 minutes than 80 minutes consistent with the expected dephosphorylation of receptor-p-Tyr. Addition of vanadate with PDGF blocked dephosphorylation of p-Tyr-proteins receptors and permitted accumulation of a large number of p-Tyr-proteins whose phosphorylation was otherwise undetectable. After 80 minutes, the p-Tyr-proteins were still evident. Also, after 80 minutes in the presence of vanadate, the 60 kDa, 125 kDa, and 180 kDa proteins showed higher levels of tyrosine phosphorylation even in the absence of PDGF. These results confirmed that vanadate treatment inhibited dephosphorylation of p-Tyr proteins generated in response to PDGF/serum signaling and suggested a possible role for p-Tyr proteins in regulation of collagen matrix contraction.

Effect of Vanadate/PDGF/Serum on the Actin Cytoskeleton

It is likely that vanadate/PDGF/serum treatment inhibits collagen matrix contraction through an effect on the actin cytoskeleton since a functional action cytoskeleton and myosin light chain kinase activity have been implicated in matrix contraction (Bell et al., 1979; Tomasek et al., 1992; Carpenter et al., 1990; Guidry et al., 1985; and Ehrlick et al., 1991). It has been reported that treatment of human fibroblasts spread on culture dishes causes redistribution of actin into lamellar membrane ruffles along the cell margins and circular ruffles on the dorsal cell surface (Mellstrom et al., 1988; Hammacher et al., 1989; and Hedberg et al., 1993), and vanadate treatment of baby hamster kidney cells has been shown to cause redistribution of F-actin into structures called podosomes (Marchisio et al., 1988).

Changes in the cytoskeletal organization of fibroblasts after treatment with PDGF and sodium vanadate were studied. Fibroblasts in monolayer culture were incubated with medium alone or with sodium vanadate (1 mM) in DME/10% FBS. FBS was CM-Sephadex treated. Ten minutes after addition of vanadate, 50 ng/ml PDGF-BB was added to some samples. After a total incubation of 20 minutes or 80 minutes, the cells were fixed, permeabilized, and stained with FITC-phalloidin. The following groups of cells were compared to each other: control cells, cells treated 80 minutes with PDGF alone, cells treated 20 minutes with sodium vanadate and PDGF, and cells treated 80 minutes with sodium vanadate and PDGF.

Actin stress fibers constitute an extensive array found in human fibroblasts spread on culture dishes. No change in cytoskeletal organization was evident when these cells were treated with vanadate/serum for up to 80 minutes. However, cells incubated with PDGF/serum for 80 minutes developed marked lamellar ruffling but no circular ruffles were seen. Cells treated with vanadate/PDGF/serum for 80 minutes, in marked contrast, appeared to undergo reorganization of the actin cytoskeleton with disappearance of stress fibers in more than 50% of the cells and organization of actin into small aggregates. These changes in the cytoskeleton were not evident after 20 minutes vanadate/PDGF/serum. Also, in the absence of serum, only 10% of the cells showed this reorganization of actin.

Under the same set of conditions, the cellular distribution of phosphotyrosine-containing proteins was determined. Most phosphotyrosine immunostaining of control fibroblasts or cells treated with PDGF/serum for 20 minutes occurred around the cell edges and appeared to be associated with focal adhesions. Treatment with vanadate/PDGF/serum, however, resulted in an overall increase in phosphotyrosine immunofluorescence, which was distributed in linear arrays parallel to the long axis of the cells. The nature of these linear arrays is unclear at present. Double immunostaining for actin and phosphotyrosine indicated only partial alignment of phosphotyrosine-containing proteins with stress fibers.

After 80 minutes, the phosphotyrosine immunostaining patterns of control and PDGF/serum-treated fibroblasts were similar to the 20 minute samples. At this time, an increased level of staining for phosphotyrosine and some linear arrays of phosphotyrosine-containing molecules could be observed in vanadate/serum-treated cells. Fibroblasts treated with vanadate/PDGF/serum for 80 minutes showed an entirely different pattern of p-Tyr immunostaining than that observed after 20 minutes. The fibrillar arrays had disappeared. Some irregularly-shaped cells appeared to be retracting their pseudopodia and had bright, uniform phosphotyrosine staining. Other cells contained numerous aggregates of phosphotyrosine, and double immunostaining indicated partial co-localization of actin and phosphotyrosine in the aggregates.

Inhibition of Wound Contraction In Vivo

Discovery of protein tyrosine phosphatase inhibitors and their role in interfering with tyrosine phosphorylation signaling pathways, has led to the development of new therapeutic approaches to wound contraction.

The compositions of the invention may be used for inhibiting wound closure and consequently reducing scar formation. The compositions work to inhibit dephosphorylation of tyrosine phosphatase receptors and to inhibit fibroblast contraction. The compositions also are prominently involved in down-regulating cell growth.

As the invention may be employed to treat various types of wounds, many types of pharmaceutical peptide formulations are contemplated. Therapeutic or pharmacological compositions of the present invention will generally comprise an effective amount of a protein tyrosine inhibitor such as a salt of vanadate dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carders include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the therapeutic compositions of the present invention.

The preparation of pharmaceutical compositions of the present invention will be known to those of skill in the art in light of the present disclosure. If desired, such compositions may be prepared as injectables, either as liquid solutions or suspensions; solid forms suitable for solution in, or suspension in, liquid prior to injection; as tablets or other solids for oral administration; and as time release capsules; or in any other form currently used, including cremes or lotions.

Solutions of the active compounds as pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile solutions suitable for injection are contemplated to be useful in treating various diseases and may be administered into the blood stream or into the precise site of the wound. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO (dimethyl sulfoxide) as solvent is preferred as this will result in extremely rapid penetration, delivering high concentrations of the active peptide, peptides or agents to a small area.

The formulation of compositions for topical use, such as in creams, ointments and gels is particularly contemplated. The preparation of oleaginous or water-soluble ointment bases is well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates. Even delivery through the skin may be employed if desired, e.g., by using transdermal patches, iontophoresis or electrotransport.

Buffered ophthalmic solutions also fall within the scope of the invention. These may be used in connection with patients recovering from eye injuries. The buffering is necessary due to pH changes the composition may cause. Ophthalmic preparations may be created in accordance with conventional pharmaceutical practice, see for example "Remington's Pharmaceutical Sciences" 15th Edition, pages 1488 to 1501 (Mack Publishing Co., Easton, Pa.).

Suitable ophthalmic preparations will generally contain a composition as disclosed herein in a pharmaceutically acceptable solution, suspension or ointment. The ophthalmic preparation will preferably be in the form of a sterile buffered solution containing, if desired, additional ingredients, for example preservatives, buffers, tonicity agents, antioxidants and stabilizers, nonanoic wetting or clarifying agents, viscosity-increasing agents and the like.

Suitable preservatives for use in such a solution include benzalkonium chloride, benzethonium chloride, chlorobutanol, thimerosal and the like. Suitable buffers include bode acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxymethylpropylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

A minimal volume of a composition required to disperse the peptide is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580).

In certain embodiments, active compounds may be administered orally. This is contemplated for agents which are generally resistant, or have been rendered resistant, to proteolysis by digestive enzymes. Such compounds are contemplated to include dextrorotatory peptides; chemically designed or modified agents; and peptide and liposomal formulations in time release capsules to avoid peptidase and lipase degradation.

Oral formulations may include compounds in combination with an inert diluent or an assimilable edible carrier; those enclosed in hard or soft shell gelatin capsules; those compressed into tablets; or those incorporated directly with the food of the diet. For oral, therapeutic administration, the active compounds may be incorporated with excipients and used in the form of ingestible tablets, buccal tablets, troches, capsules, elixirs, suspensions, syrups, wafers, and the like. Such compositions and preparations should generally contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of In Vitro Models for the Study of Wound Contraction and Initiation of Contraction Fibroblasts from human foreskin specimens were maintained in a 75 cm$^2$ tissue culture flask in Dulbecco's modified Eagle's medium (DME, GIBCO) supplemented with 10% fetal bovine serum (FBS) (Intergen Company, Purchase, N.Y.). Monolayer cultures were established by placing 1×10$^5$ cells per well in Coster 6-well plates. Hydrated collagen matrices were prepared from Vitrogen "100" collagen (Celtrix Labs, Palo Alto, Calif.). Neutralized collagen solutions (1.5 mg·ml) contained fibroblasts in DME but no serum. Aliquots (0.2 ml; 1×10$^5$ cells) of the cell/collagen mixtures were prewarmed to 37° C. for 3–4 minutes and then placed in Costar 24-well culture plates. Each aliquot occupied an area outlined by a 12 mm diameter circular score within a well.

Polymerization of collagen matrices required 60 minutes at 37° C., after which 1.0 ml of DME/10% fetal bovine serum and 50 ug/ml ascorbic acid were added to each well. Fresh medium with 1% instead of 10% fetal bovine serum was added to both monolayer culture and collagen matrices after 24 hr, and the cultures were incubated for 4 days. During this culture period, fibroblasts reorganized the anchored matrices, developed mechanical stress, and differentiated into cells resembling myofibroblasts (Mochitate et al., 1991; Tomasek et al., 1992; and Lee et al., 1993). Contraction of myofibroblast-like cells in the stressed matrices was initiated by releasing the matrices from the underlying culture dish with a spatula, and in most cases contraction was measured within the first hour after release.

In some experiments, contraction was measured immediately after matrices were polymerized before fibroblasts developed stress. In the case of this so-called "floating collagen matrix" contraction, the extent of contraction was measured after 4 hours.

Matrix contraction was terminated by fixing cells with 3% paraformaldehyde in Dulbecco's phosphate-buffered Saline (DPBS) (150 mM NaCl, 3 mM Kcl, 1 mM KH$_2$HPO$_4$, 1 mM CaCl$_2$, 0.5 mM MgCl$_2$, pH 7.2) for 10 minutes at 22° C. The matrices were washed, placed on a glass slide, and diameters were measured with a ruler. Percent contraction was calculated as: 100×(12 mm final diameter)/12 min.

In the contraction experiments, cells were treated with various combinations of sodium vanadate (Fisher Scientific), human recombinant PDGF-BB (Upstate Biotechnology Inc.), epidermal growth factor (Upstate Biotechnology Inc.), and lysophosphatidic acid (Sigma). Except for the experiments depicted in FIG. 4 and FIG. 5, fetal bovine serum used during the contraction incubations was first passed through a CM-Sephadex column as a precaution to remove any PDGF that might be present in the serum (Vogel et al., 1978), and the protein concentration of CM-Sephadex-treated fetal bovine serum was adjusted to match the original fetal bovine serum preparation.

EXAMPLE 2

Immunoblotting

Extracts from cells in collagen matrices were prepared by scraping matrices into 0.1 ml (per matrix) of 0.2% NP-40 in DPBS containing proteinase inhibitors (1 ug/ml pepstatin A, 1 ug/ml leupeptin, 14-(2-aminoethyl)-benzene-sulfonylfluoride HCl) and phosphatase inhibitors (2 mM sodium orthovanadate, 50 mM sodium fluoride, 1 mM ammonium molybdate). Samples were homogenized (50 strokes) with a 1 ml Dounce homogenizer (Wheaton, B pestle) at 4° C., and collagen fibrils and nuclei were removed by centrifugation at 11,000×G (Beckman Microfuge) for 5 min. To compare extracts from different cultures, samples were normalized to constant cell numbers by measuring lactate dehydrogenase activity as described previously (Lin et al., 1993). Samples to be subjected to SDS-PAGE were dissolved in reducing SDS sample buffer (62.5 mM Tris, 2% SDS, 10% glycerol, 0.01% bromophenol blue, 5% mercaptoethanol, pH 6.8).

Samples for immunoblotting were subjected to electrophoresis in 9% acrylamide mini-slab gels (Laemmli, 1970), and transferred to PVDF membranes. After blocking the membranes with 76 mM Na phosphate, 68 mM NaCl, 6% casein, 1% polyvinylpyrrolide 40 (PVP-40), 3 mM NAN$_3$, and 10 mM EDTA for 3 hours, the membranes were incubated for 2 hours with anti-p-Tyr mAb (Upstate Biotechnology Inc.) in blocking solution. At the end of incubations, the blots were washed with 0.3% between 20, 76 mM Na phosphate and 68 mM NaCl followed by incubation for 1 hour with alkaline phosphatase-conjugated goat anti-mouse antibodies in blocking solution. Photoactivation was initiated by addition of 50 mM sodium bicarbonate (pH 9.6), 1 mM $MgCl_2$ and disodium-3-(4-methoxyspire{1,2-dioxetane-3,2'-(5'chloro)tricyclo-[3.3.1.13,7]decan}-4-yi) phenyl phospate (CSPD). Light emitted by activated CSPD was detected with Kodak XAR x-ray film.

EXAMPLE 3

Immunofluorescence Microscopy

Cultures were fixed for 10 minutes at 22° C. with 3% paraformaldehyde in DPBS. To block non-specific staining, the samples were treated with 1% glycine and 1% BSA (bovine serum albumin). (Fraction V, ICN Biochemicals Inc.) for 30 min. Subsequently, the cultures were permeabilized with 0.2% NP-40 in Dulbecco's phosphate-buffered saline for 10 min. Samples were incubated with anti-p-Tyr monoclonal antibody (Sigma) in DPBS containing 1% BSA for 1 hour at 37° C. washed 3 times, and then incubated with RITC-conjugated goat anti-mouse antibodies (Zymed laboratories). For actin staining, samples were labeled with 1 unit FITC-conjugated phalloidin (Molecular Probes) for 30 minutes at 37° C. After washing, the samples were mounted with glycerol/PBS (9:1) containing 0.001% phenylenediamine, and examined and photographed with a Zeiss Universal phase contract microscopy.

EXAMPLE 4

Inhibition of Stressed Collagen Matrix Contraction by PDGF and Vanadate

Sodium vanadate was added at the concentrations indicated in FIG. 1 to fibroblasts in stressed collagen matrices in DME/10% FBS. Ten minutes after addition of vanadate, 50 ng/ml PDGF-BB was added to the designated samples. Ten minutes later, contraction was initiated when matrices were released from the substratum, and the extent of contraction was measured 1 hour later. FBS was CM-Sephadex treated.

EXAMPLE 5

Lag Period Required for Inhibition of Matrix Contraction

During the pretreatment period, sodium vanadate (1 mM) was added to fibroblasts in stressed collagen matrices in DME/10% FBS. Ten minutes after addition of vanadate, 50 ng/ml PDGF-BB was added to the samples. Part (A) of FIG. 2 shows an experiment where the matrices were washed after a total incubation of 20 minutes and switched to DME/10 FBS lacking sodium vanadate and PDGF-BB. The contraction was initiated by releasing the matrices, and the extent of contraction was measured 1 hour later. Part (B) of FIG. 2 shows an experiment where the cells were washed after a total incubation of 80 minutes and switched to DME/10% FBS lacking sodium vanadate and PDGF-BB. Then contraction was initiated and measured as above. Part (C) of FIG. 2 shows an experiment where the cells were washed after a total incubation of 20 minutes and switched to DME/10% FBS lacking sodium vanadate and PDGF-BB and incubated for an additional 60 minutes. Then contraction was initiated and measured as above.

EXAMPLE 6

Requirement for Serum During the Pretreatment Period

During the pretreatment period, sodium vanadate (1 mM) was added to fibroblasts in stressed collagen matrices in DME containing FBS at the concentrations designated. Ten minutes after addition of vanadate, 50 ng/ml PDGF-BB was added. After a total incubation of 80 minutes, the cells were washed and switched to fresh medium containing 10% FBS. Then contraction was initiated, and the extent of contraction was measured 1 hour later. FBS was CM-Sephadex treated.

EXAMPLE 7

Effect on Serum, Lysophosphatidic Acid, and PDGF on Contraction of Collagen Matrices The contraction medium was DME containing 10% FBS, 0.05 mg/ml lysophosphatidic acid, or 50 ng/ml PDGF-BB as indicated in FIG. 4, and the extent of contraction was measured after 1 hour for stressed matrices and after 4 hours for floating matrices.

EXAMPLE 8

Specificity of Inhibition

During the pretreatment period, sodium vanadate (1 mM) was added where indicated to fibroblasts in stressed collagen matrices. The medium was DME containing 10% FBS, 200 ng/ml epidermal growth factor, or 0.05 mg/ml lysophosphatidic acid as indicated in FIG. 5. Ten minutes after addition of vanadate, 50 ng/ml PDGF-BB, 200 ng/ml epidermal growth factor, or 0.05 mg/ml lysophosphatidic acid were added to the designated samples. After a total incubation of 80 minutes, the samples were washed and switched to DME/10% FBS. Then contraction was initiated, and the extent of contraction was measured 1 hour later. FBS was CM-Sephadex treated.

EXAMPLE 9

Inhibition of Boating Matrix Contraction by Vanadate and PDGF

Collagen matrices containing fibroblasts as indicated were polymerized for 1 hour. The medium was switched to DME/10% FBS with sodium vanadate (1 mM) added as indicated in FIG. 6. Ten minutes, 50 ng/ml PDGF-BB was added to the designated samples. After an additional 10 minutes, contraction was initiated by releasing the matrices from the substratum, and the extent of contraction was measured 4 hours later.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Bell, E., Ivarsson, B. and Merrill, C. (1979) *Proc. Nat. Acad. Sci. USA* 76:1274–1278.

Bixby, I. L. and Jhabvala, P. (1992) *J. Neurobiol.* 23:468–480.

Bockus, B. J. and Stiles, C. D. (1984) *Exp. Cell Res.* 153:186–197.

Carpenter, G. and Cohen, S. (1990) *J. Biol. Chem.* 265:7709–7712.

Clark and P. M. Henson, Plenum Press NY, pp 3–33.

Clark, R. A. F., Folkvord, J. M., Hart, C. E., Murray, M. J. and McPherson, J. M. (1989) *J. Clin. Invest.* 84:1036–1040.

Clark, R. A. F. (1988) In: *The Molecular and Cellular Biology of Wound Repair.* Ed: R. A. F. Darby, I. and Gabbiani, G. (1990) *Lab. Invest.* 63:21–29.

Eddy, R. J., Petro, J. A. and Tomasek, I. I. (1988) *Am. J. Pathol.* 130:252–260.

Edwards. J. G., Campbell, G., Grierson, A. W. & Kinn, S. R. (1991) *J. Cell Sci.* 98:363–368.

Ehrlich, H. P., Rockwell, W. B., Cornwell, T. L. and Rajaratnam, I. B. M. (1991) *J. Cell Physiol.* 146:1–7.

Fischer, E. H., Charbonneau, H. and Tonks, N. K. (1991) *Science* 253:401–406.

Gordon, J. A. (1991) *Meth. Enzymol.* 201:477–482.

Grinnell, F. (1994) *J. Cell Biol.* 124:401–404.

Harris, A. K., Stopak, D. and Wild, P. (1981) *Nature* 290:249–251.

Guidry, C. and Grinnell, F. (1985) *J. Cell Sci.* 79:67–81.

Gullberg, D., Tingstrom A., Thuresson, A-C., Olsson, L., Terracio, L., Borg, T. K. and Rubin, K. (1990) *Exp. Cell Res.* 186:264–272.

Hammacher, A., Mellstrom, K. Heldin, C-H. and Westermark, B. (1989) *EMBO J.* 8:2489–2495.

Hedberg, K. M., Bengtsson, T., Safiejko-Mroczka, B., Bell, P. B. and Lindroth, M. (1993) *Cell Motil & Cyto.* 24:139–149.

Heffetz, D. Rutter, W. J. and Zick, Y. (1992) *Biochem. J.* 288:631–635.

Herman, B. and Pledger, W. J. (1985) *J. Cell Biol.* 100:1031–1040.

Hordijk, P. L., Verlaan, I., Van Corven, E. J. and Moolenaar, W. H. (1994) *J. Biol. Chem.* 269:645–651.

Hunt, T. K. and Dunphy, J. E. (1979) *Fundamentals of Wound Management.* Appleton-Century-Crofts, New York.

Kolodney, M. S. and Elson, E. L. (1993) *J. Biol. Chem.* 268:23850–23855.

Kolodney, M. S. and Wysolmerski, R. B. (1992) *J. Cell Biol.* 117:73–82.

Laemmli, U.K. (1970) *Nature* 227:680–685.

Lee, T-L., Lin, Y-C., Mochitate, K. and Grinnell, F. (1993) *J. Cell Sci.* 105:165–177.

Lin, Y-C. and Grinnell, F. (1993) *J. Cell Biol.* 122:663–672.

Madsen, K. L., Ariano, D., and Sedorak, R. N. (1995) *Diabetologia* 38:403–412.

Marchisio, P. C., D'Urso, N., Comoglio, P. M., Giancotti, F. G. and Tarone, G. (1988) *J. Cell. Biochem.* 37:151–159.

Mast, B. A. (1992) In: *Wound Healing: Biochemical and Clinical Aspects.* Ed: I. K. Cohen, R. F. Dieglemann, and W. J. Lindblad, W. B. Saunders Co., Philadelphia, Pa., pp 344–355.

Mellstrom, K., Heldin, C-H. and Westermark, B. (1988) *Exp. Cell Res.* 177:347–359.

Mochitate, K. Pawelek, P. and Grinnell, F. (1991) *Exp. Cell Res.* 193:198–207.

Morgan, C. J. and Pledger, W. J. (1992) In: *Wound Healing: Biochemical and Clinical Aspects.* Ed: I. K. Cohen, R. F. Diegelmann, and W. J. Lindblad, W. B. Saunders Co., Philadelphia, Pa., pp. 63–76.

Nakagawa, S., Pawelek, P. and Grinnell, F. (1989) *Exp. Cell Res.* 182:572–582.

Nishiyama, T., Akutsu, N., Horii, I., Nakayama, Y., Ozawa, T. and Hayashi, T. (1991) *Matrix* 11:71–75.

Parker, R. D., and Sharma, R. P. (1978) *Jrnl. of Envir. Ethol and Tox.* 2:235–245.

Peacock, E. E. (1984) *Wound Repair* 3rd Edition, W. B. Saunders Co., Philadelphia.

Pilcher, B. K., Kim, D. E., Carney, D. H. and Tomasek, J. J. (1994) *Exp. Cell Res.* 211:368–373.

Rankin, S. and Rozengurt, E. (1994) *J. Biol. Chem.* 269:704–710.

Ridley, A. J. and Hall, A. (1992) *Cell* 70:389–399.

Ridley, A. J. and Hall, A. (1994) *EMBO J.* 13:2600–2610.

Roeckel, D. and Krieg, T. (1994) *Exp. Cell Res.* 211:42–48.

Rudolph, R., Berg, J. V. and Ehrlick, H. P. (1992) In: *Wound Healing: Biochemical and Clinical Aspects.* Ed: I. K. Cohen, R. F. Diegelmann, and W. J. Lindblad, W. B. Saunders Co., Philadelphia, Pa., pp 96–114.

Saville, M. K., Graham, A., Malarkey, K., Paterson, A., Gould, G. W., and Plevin, R. (1994) *Biochem. J.* 301:407–414.

Seufferlein, T. and Rozengurt, E. (1994) *J. Biol. Chem.* 269:9345–9351.

Skalli, O. and Gabbiani, G. (1988) In: *The Molecular and Cellular Biology of Wound Repair.* Ed: R. A. F. Clark and P. M. Henson, Plenum Press NY, pp 373–402.

Tidball, J. G. and Spencer, M. J. (1993) *J. Cell Biol.* 123:627–635.

Tomasek, J. J., Haaksma, C. J., Eddy, R. J. and Vaughan, M. B. (1992) *Anatomical Record* 232:359–368.

Tringstrom, A., Heldin, C-H. and Rubin, K. (1992) *J. Cell Sci.* 102:315–322.

Ullrich, A. and Schlessinger, J. (1990) *Cell* 61:203–212.

Vogel, A., Raines, E., Kariya, B., Rivest, M. J. & Ross, R. (1978) *Proc. Natl. Acad. Sci. USA* 75:2810–2814.

Volberg, T., Zick, Y., Dror, R., Sabanay, I., Gilon, C., Levitzki, A. and Geiger, B. (1992) *EMBO J.* 11:2733–1742.

Welch, M. P., Odland, G. F. and Clark, R. A. F. (1990) *J. Cell Biol.* 110:133–145.

We claim:

1. A method of inhibiting fibroblast contraction in a collagen matrix comprising exposing said matrix to an effective amount of a tyrosine phosphatase inhibitor in the presence of serum and platelet-derived growth factor.

2. The method of claim 1 wherein said tyrosine phosphatase inhibitor is a salt of vanadate.

3. The method of claim 1 wherein said matrix is exposed to said tyrosine phosphatase inhibitor in a medium in which said serum concentration is between approximately 0.5 percent and 10 percent of the medium.

4. The method of claim 1 wherein said matrix is exposed to said tyrosine phosphatase inhibitor in a medium in which said serum concentration is approximately 10 percent of the medium.

5. The method of claim 1 wherein said method of inhibiting fibroblast contraction comprises administering to an animal a therapeutically effective amount of a tyrosine phosphatase inhibitor dispersed in a pharmacologically acceptable carrier.

6. The method of claim 5 wherein said tyrosine phosphatase inhibitor is administered to a wound through topical application.

7. The method of claim 5 wherein said tyrosine phosphatase inhibitor is administered to a wound through parenteral administration.

8. The method of claim 5 wherein said tyrosine phosphatase inhibitor is administered to a wound through oral administration.

9. The method of claim 5 wherein a therapeutically effective amount is the amount required to achieve a blood serum level of between 3.0 and 15.0 micromolar.

10. The method of claim 1 wherein said collagen matrix is in a wound and said wound is exposed to an effective amount of said tyrosine phosphatase inhibitor so as to inhibit contraction of said wound.

* * * * *